(12) United States Patent
Wielsch et al.

(10) Patent No.: US 6,897,955 B2
(45) Date of Patent: May 24, 2005

(54) ELLIPSOMETER

(75) Inventors: Uwe Wielsch, Berlin (DE); Michael Arena, Berlin (DE); Uwe Richter, Wernsdorf (DE); Georg Dittmar, Berlin (DE); Albrecht Kruger, Berlin (DE); Helmut Witek, Krailing (DE)

(73) Assignee: Sentech Instruments GmbH, Berlin (DE)

( * ) Notice: Subject to any disclaimer, the term of this patent is extended or adjusted under 35 U.S.C. 154(b) by 0 days.

(21) Appl. No.: 10/276,353
(22) PCT Filed: May 10, 2001
(86) PCT No.: PCT/DE01/01807
§ 371 (c)(1),
(2), (4) Date: Jun. 10, 2003
(87) PCT Pub. No.: WO01/86257
PCT Pub. Date: Nov. 15, 2001

(65) Prior Publication Data
US 2004/0090626 A1 May 13, 2004

(30) Foreign Application Priority Data
May 10, 2000 (DE) ........................................ 100 23 477

(51) Int. Cl.⁷ .................................................. G01J 4/00
(52) U.S. Cl. ........................................ 356/369; 356/367
(58) Field of Search ................................ 356/364–369, 356/67; 250/201.2, 201.6, 225

(56) References Cited

U.S. PATENT DOCUMENTS

| 3,880,524 A |   | 4/1975  | Dill et al.     |         |
|-------------|---|---------|-----------------|---------|
| 4,671,660 A | * | 6/1987  | Distl et al.    | 356/367 |
| 5,166,752 A | * | 11/1992 | Spanier et al.  | 356/369 |
| 5,793,480 A | * | 8/1998  | Lacey et al.    | 356/73  |
| 5,910,841 A | * | 6/1999  | Masao           | 356/369 |
| 5,910,842 A | * | 6/1999  | Piwonka-Corle et al. | 356/369 |
| 5,955,139 A | * | 9/1999  | Iturralde       | 427/9   |
| 6,060,237 A | * | 5/2000  | Nygren et al.   | 435/6   |
| 6,275,291 B1 |  | 8/2001  | Abraham et al.  |         |
| 6,307,627 B1 | * | 10/2001 | Vurens         | 356/369 |

FOREIGN PATENT DOCUMENTS

| DE | 24 30 521 A1  | 1/1975  |
| DE | 196 22 212 C1 | 12/1997 |
| DE | 197 08 036 A1 | 9/1998  |
| DE | 198 42 364 C1 | 4/2000  |
| JP | 11173994 A    | 7/1999  |
| JP | 11 173994     | 7/1999  |

OTHER PUBLICATIONS

International Search Report of PCT/DE01/01807, dated Dec. 28, 2001.
International Preliminary Examination Report of PCT/DE01/01807, dated Oct. 15, 2002.
Patent Abstract of Japan, Publication No. 11173994, Published on Jul. 2, 1999, in the name of HDI Instrumentation.
English translation of International Preliminary Examination Report of corresponding PCT/DE01/01807, dated Oct. 15, 2002.

* cited by examiner

Primary Examiner—Michael P. Stafira
(74) Attorney, Agent, or Firm—Christie, Parker and Hale, LLP

(57) ABSTRACT

This invention concerns an ellipsometer for the examination of a sample whereby the ellipsometer has a broadband light source on the emitter side and a detector on the receiver side for a receiver light beam reflected from the sample. A refractive optic for the generation of a measuring spot on the sample and an aperture arranged on the emitter side for the definition of a measuring spot on the sample. The spectroscopic ellipsometer of the present invention makes it possible to easily produce a precisely defined measuring spot on the sample.

45 Claims, 4 Drawing Sheets

ELLIPSOMETER

CROSS-REFERENCE TO RELATED APPLICATION

This application is a National Phase Patent Application of International Application Number PCT/DE01/01807, filed on May 10, 2001, which claims priority of German Patent Application Number 100 23 477.1, filed May 10, 2000

BACKGROUND OF THE INVENTION

The invention relates to an ellipsometer for the examination of a sample.

Ellipsometers are used as optical measuring devices to determine the physical parameters of samples. For this, a light beam is directed onto a sample, enabling the characteristics of the sample to be obtained due to the change in the polarization of the light upon reflection from the sample or the transmission through the sample. In particular, ellipsometry allows very thin film layers and film thicknesses as well as indices of refraction of the samples to be determined. This is particularly important in wafer production for integrated circuits.

Due to the increased integration level of these wafers, it is necessary to evaluate sample characteristics on increasingly smaller measuring surfaces. For this reason, generating a small measuring spot is an important characteristic of ellipsometers.

To obtain the most comprehensive information possible regarding the characteristics of the samples, spectroscopic ellipsometers with polychromatic light sources instead of monochromatic ellipsometers are increasingly used. This method has the disadvantage that with known systems, it is difficult to focus polychromatic light on a small measuring spot.

Ellipsometers that use reflective optics (mirror systems) for focusing are known, in which complex beam paths develop regularly. Furthermore, the use of mirror systems results in a non-centralized (off-axis) beam path that in turn results in geometric errors during imaging.

SUMMARY OF THE INVENTION

In one embodiment, the present invention is a spectroscopic ellipsometer that allows sample characteristics to be determined in a small measuring spot within a very short period of time and with high precision.

The ellipsometer of the present invention uses a refractive optic (lens system) to generate a measuring spot that is as small as possible. Compared with mirror systems, this method has simpler beam paths. Also, in a lens system, the emitter light beam can be directed such that it passes through the optics at a very limited angle. Thus, the impact on the measuring values is minimized. Also, a refractive optic avoids displacement of the beam path (off-axis beam path).

A limited emitter light beam is formed from the light that is emitted from the light source by using an aperture, which is disposed on the emitter side of the ellipsometer.

Particularly, an emitter lens system for focusing the light beam onto the sample has an aperture such that at least the first diffraction order is detected downstream from the aperture. This improves the quality of the focus on the sample.

One embodiment of the ellipsometer of the present invention has an emitter lens system and/or a receiver lens system with at least one achromatic lens system. Its achromatic nature prevents a distortion of the measurements generated with polychromatic light and yields a measuring spot whose size does not depend on the wavelength.

In another embodiment of the ellipsometer of the present invention, the emitter lens system and/or the receiver lens system is designed and built such that the ellipsometric angles PSI and DELTA in an arrangement of the ellipsometer arms at 90° respectively (relative to the normal of the sample, that is, in the transmitted light position) are influenced only below the precision limit of the ellipsometer by inserting at least one lens system when the aperture of at least one lens system is fully illuminated.

Another embodiment of the ellipsometer of the present invention has a means for focusing a hot spot of the light source onto the plane of a lens of the emitter lens system.

The aperture and the emitter lens system generate a small measuring spot on the sample. It is particularly advantageous when the opening of the aperture is directed to a hot spot of the light source. The emitter characteristic of a hot spot as opposed to the illuminating margin areas of a polychromatic light source is especially stable, i.e., fluctuations in intensity are particularly minor.

In an embodiment of the invention, the aperture has a rectangular opening. Such an opening can be easily built.

The opening of the aperture has adjustable geometry and/or size such that the aperture can be adjusted to various lamps or operating states.

The longest axis of the opening of the aperture is perpendicular to the incidence plane of the emitter light beam on the sample, such that a square measuring spot can be generated.

The longest axis of the opening of the aperture is arranged in parallel or perpendicular to the connecting line of the electrodes, thus obtaining particularly stable emitter characteristics.

At least one retarder for the phase shift of the emitter light beam and/or receiver light beam can be pivoted into or is permanently arranged in the corresponding light path. It is also advantageous if the retarder is achromatic. It is particularly advantageous if the at least one retarder is rotatable.

In another embodiment of the ellipsometer of the present invention at least one grey filter is pivotable into the emitter light beam for intensity regulation. Thus, the ellipsometer can be adjusted to various reflection coefficients of samples.

An adjustable first polarization optic is arranged on the emitter side and/or an adjustable second polarization optic is arranged on the receiver side of the ellipsometer of the present invention. Especially due to the arrangement of the polarization optics on the emitter and/or receiver side, the polarization of the light beam can be selected depending on the sample such that the measuring accuracy is increased.

The first polarization optic and/or the second polarization optic has a beam deflection of less than 15 arc seconds.

In another embodiment of the ellipsometer of the present invention, the first polarization optic and/or the second polarization optic can optionally be moved in different measuring modes, in particular continuously with constant rotation speed or with measurements at various predetermined positions. In the latter case, particularly if the samples have low reflectivity, it is possible to obtain better measuring results.

An embodiment of the ellipsometer of the present invention has a second aperture behind the receiver lens system for the selection of the incidence angle of the reflected light beam. Thus, it is possible to selectively analyze the characteristics of specific light beams.

The second aperture has an opening with a rectangular cross-section, and the longest axis of the opening of the second aperture is arranged perpendicular to the incidence plane.

In another embodiment of the ellipsometer of the present invention, the detector for the receiver light beam that is reflected by the sample is coupled to a spectrometer, with the entrance slit of the spectrometer arranged perpendicular to the longest axis of the opening of the second aperture. This allows the maximum spectral resolution of the receiver light beam.

In one embodiment, the spectrometer images the entrance slit in the detector plane, particularly retaining the image in the longitudinal direction of the entrance slit as well. Also, an optical system is provided that images the entrance slit in the detector plane. Multi-angle measuring is then possible with an appropriate detector.

In another embodiment of the ellipsometer of the present invention, the imaging of the entrance slit in the detector plane takes place by means of a dispersive element of the spectrometer itself, resulting in a particularly simple construction.

For multi-angle analysis, one embodiment of the ellipsometer of the present invention includes a two-dimensional detector for the evaluation of angle-dependent data. Preferably, the detector has a two-dimensional FFT CCD (full frame transfer charged coupled device), a matrix of single diodes, PMTs (photomultiplier tubes) or at least two one-dimensional photo diode arrays. This embodiment allows precise multi-angle measurements.

The detector for the receiver light beam reflected by the sample is coupled to a grid spectrometer, the grid being arranged such that the grid lines are perpendicular to the longest axis of the second aperture imaged in the beam direction. In another embodiment of the ellipsometer of the present invention, a means for correction of the polarization sensitivity of the detector and/or the spectrometer is provided. In particular, a quartz sample or a sample with a phase shift near 0° or near 180° is used. Thus, the ellipsometer of the present invention can be calibrated on site.

In addition, it is possible to use the ellipsometer as a discrete wavelength ellipsometer with a laser as a light source, with the beam of the laser using the same path as the broadband light beam (emitter/receiver light beam) of the ellipsometer of the present invention. In this embodiment, the laser beam is reflected into the light path of the ellipsometer by a beam splitter. Simultaneous use of a polychromatic and monochromatic light source increases the quality of the measurement.

The beam splitter is fixedly mounted in the beam path and an aperture construction switches between the laser beam of the discrete wavelength ellipsometer and the broadband light beam.

An embodiment of the ellipsometer of the present invention has a low-noise detector that is pivotable into the receiver light beam or coupled to the receiver light beam via a beam splitter.

The laser beam of the discrete wavelength ellipsometer can also be used to adjust the ellipsometer.

An embodiment of the ellipsometer of the present invention has at least one sensor that is arranged in the emitter beam path and/or the receiver beam path to check the intensity and position of the light source. This sensor is used to determine the spatial position of the light source. This sensor is advantageously arranged behind the first aperture.

Another embodiment of the ellipsometer of the present invention has at least one manual or automatic changer for at least one light source. The changer with a light source facilitates the exchange of the lamp, because one light source can be easily removed from the beam path of the ellipsometer. In the case of a changer with more than one light source, it is possible to move different light source into the beam path of the ellipsometer if one light source fails, for example. Thus, continuous operation of the ellipsometer can be ensured. Also, the intervals between the necessary interventions into the device are increased considerably. The changer may have a revolving stage.

To minimize or completely eliminate the efforts for calibration of the light sources, at least one light source of the changer is pre-calibrated.

The changer provides a manually or automatically adjustable reflector for the respective active light source. Thus, the light that is not diffused into the direction of the beam path of the respective active light source is deflected in the direction of the beam path of the ellipsometer.

Another embodiment has a means for automatic control of the respective active light source, in particular a power supply. Thus, the respective light source active in the beam path can, for example, be switched on and off.

In one embodiment, the ellipsometer of the present invention has a positioning means for the manual or automatic spatial positioning of at least one light source relative to the light path. Thus, a precisely defined orientation of the light source is constantly guaranteed. It is particularly advantageous for the positioning means to have a three-axis test table.

Also, the spatial position of at least one light source and/or the reflector is adjustable based on at least one regulating variable. Thus, the light source can be adapted to the measurement conditions. It is advantageous if at least one regulating variable for measuring the light intensity is generated by the sensor. If the intensity sensor is in the emitter light path in front of the sample, the lamp position can be controlled—independent of the sample—via the maximum intensity. When a sample is calibrated such that ellipsometric measuring is possible, it is also possible to use the intensity signal of the ellipsometer detector or a variable derived therefrom as a regulating variable.

In another embodiment of the ellipsometer of the present invention, a light source is reflected into the light path by at least one mirror such that the light source is perpendicular to it.

BRIEF DESCRIPTION OF THE DRAWINGS

The invention is described in detail below with reference to several exemplary embodiments in the figures of the accompanying drawings.

DESCRIPTION OF THE INVENTION

Figure 1:
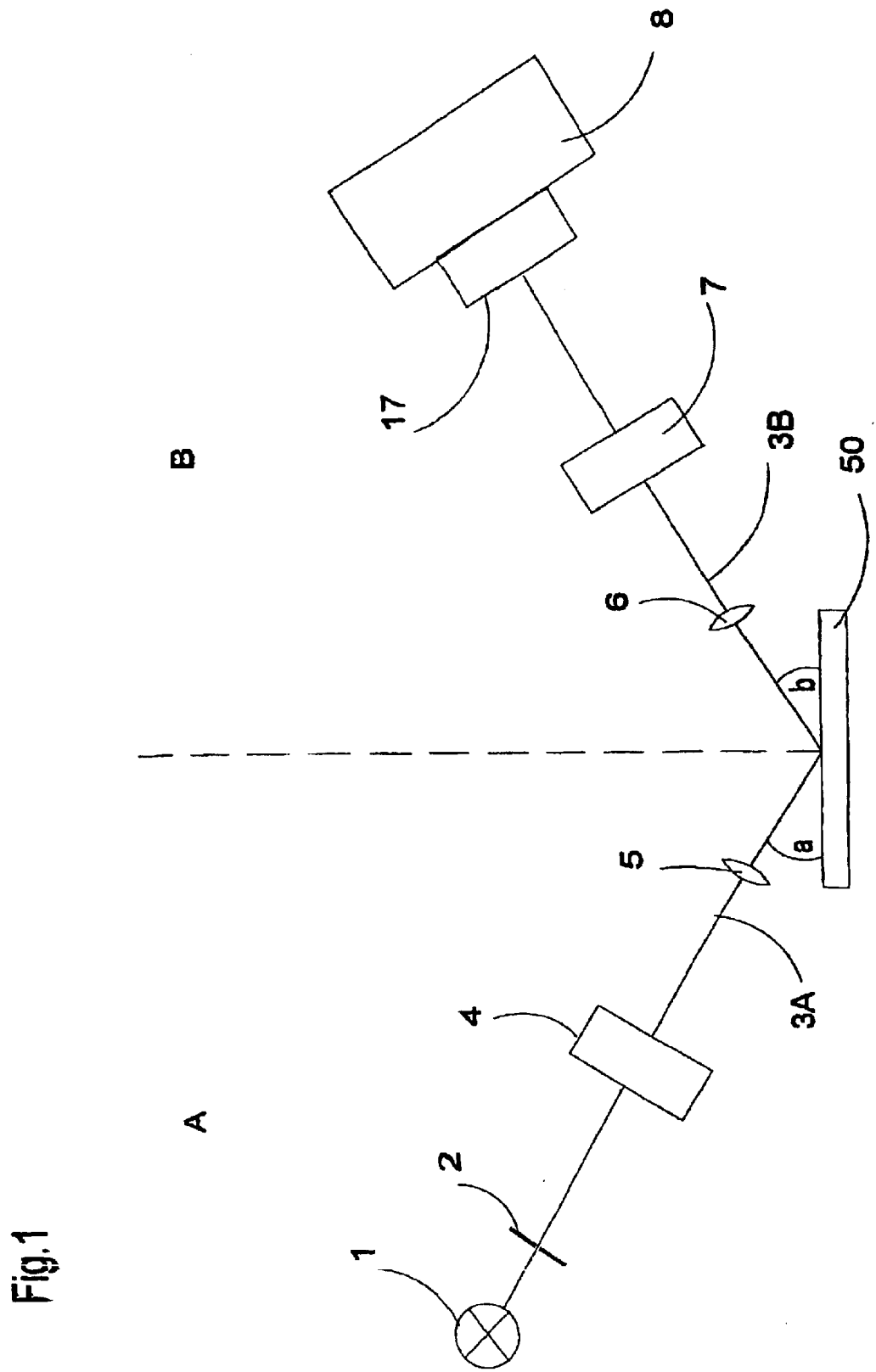
FIG. 1 is a schematic view of the basic design of an ellipsometer according to one embodiment of the present invention.

FIG. 1 is a schematic view of the basic design of an ellipsometer according to the present invention.

Since ellipsometers are known per se, only the components that are significant for the invention are described here.

Basically, an ellipsometer comprises an emitter side A and a receiver side B. On the receiver side A, a light source 1 that directs an emitter light beam 3A onto a sample 50 is arranged. From sample 50, the light is reflected as a receiver light beam 3B and recorded by a detector 8. Incidence angle a and reflection angle b are located in one plane, the incidence plane.

In this case, light source 1 is a broadband (polychromatic) light source, i.e., it emits light over a wavelength range. This range can comprise ultraviolet light, visible light and/or infrared light. A xenon lamp can be the source for white light.

Figure 3:
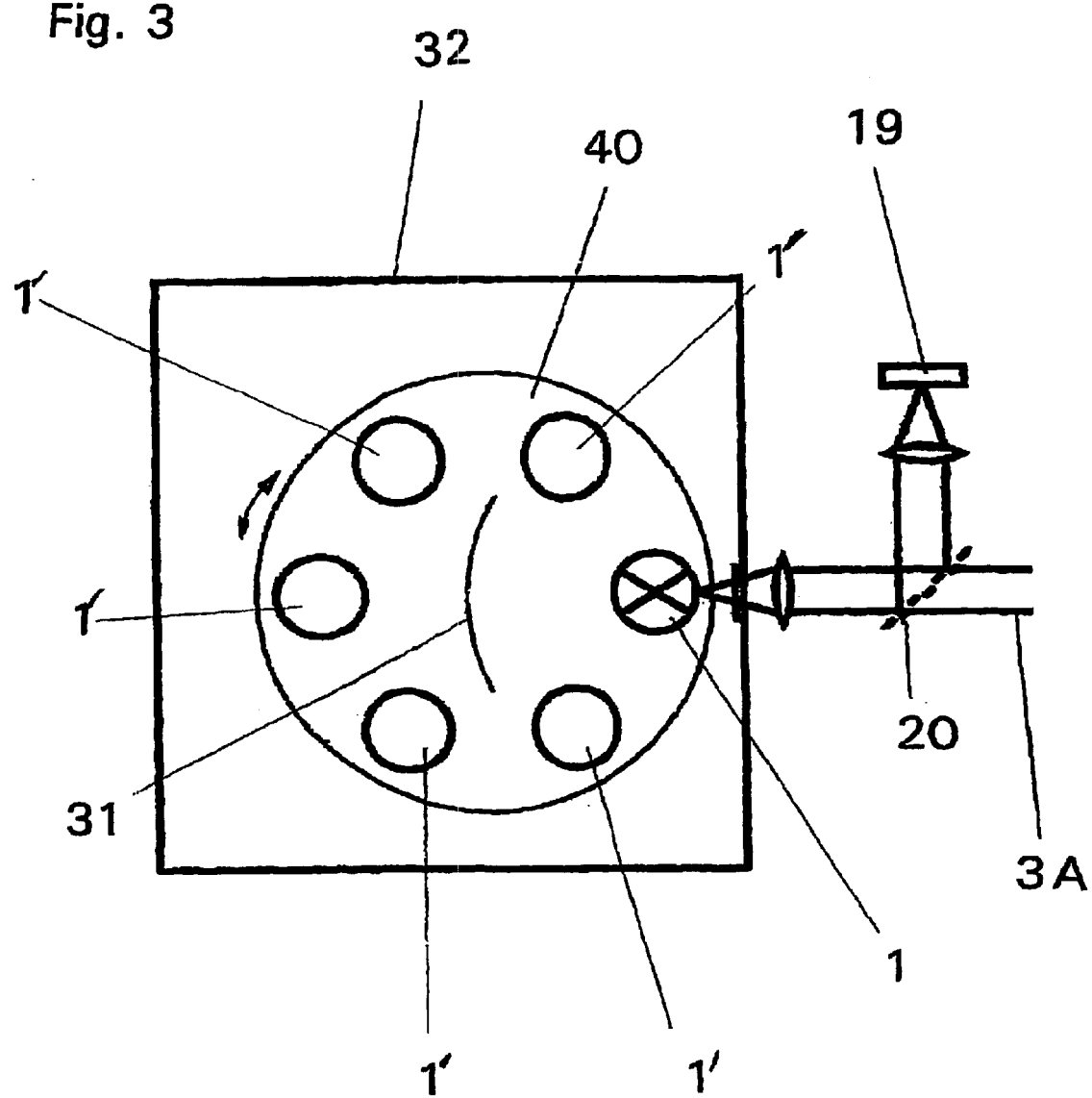
FIG. 3 is a schematic top view of a changer for light sources of the ellipsometer of the present invention.
Figure 4:
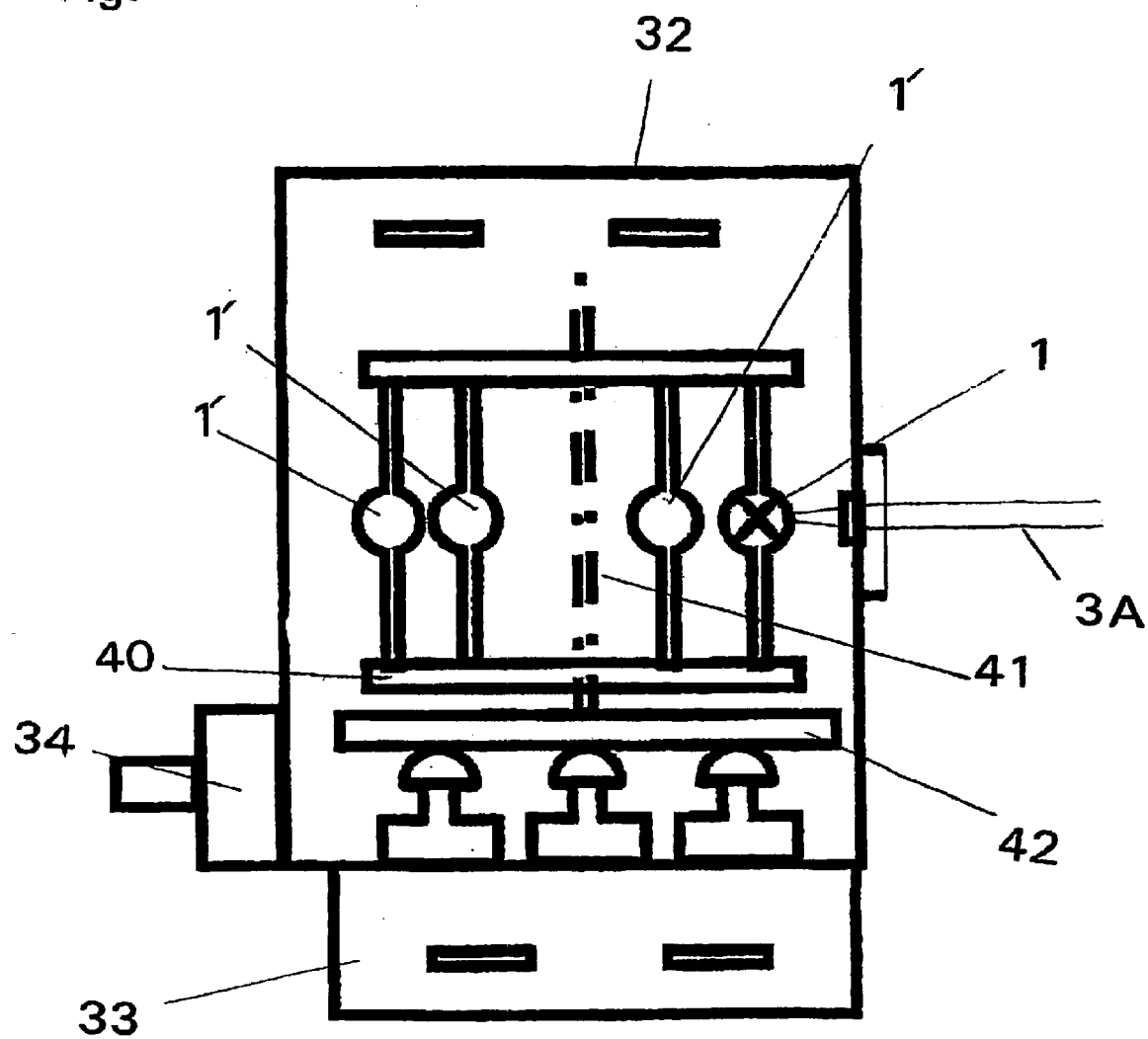
FIG. 4 is a schematic view of a changer with a test table.

Light source 1 is arranged in a lamp changer (not shown), which makes use of light sources of different characteristics in the ellipsometer, depending on the desired purpose. In continuous operation it is even possible to exchange light sources automatically after a certain period of time or if they fail. This type of light exchanger is shown in FIGS. 3 and 4.

In such a lamp changer, at least two xenon lamps are arranged on a motorized rotary table, with one xenon lamp serving as light source 1. Control or regulation of the rotary table is used to adjust one xenon lamp relative to the coupling optics into the beam path of the emission arm. In principle, it is also possible to operate the rotary table manually.

The rotary table is arranged on a controllable, motorized platform that is movable in all three directions in space, i.e., the light source is freely movable in a certain spatial area. The exact spatial position of light source 1 can be established using this platform. In particular, both the height and inclination of light source 1 can be adjusted.

A light-sensitive sensor 19, arranged behind first aperture 2, is used to control the movement of the platform and thus the position of light source 1. In an alternative embodiment, a control device receives data from position-sensitive detectors in the area of light source 1. A combination of light sensor and position detector is also possible. The signals of sensor 19 and/or the position detector provide the necessary data to readjust the respective light source 1 spatially relative to emitter beam path 3A.

Aperture 2 serves as a field aperture to define the size and shape of the measuring spot on the sample.

In the present case, first aperture 2 has a rectangular opening that is arranged perpendicular to the incidence plane. It is possible to use a first aperture 2 with a different opening geometry or with a variable opening geometry.

The broadband light sources 1 that are used here have a non-homogenous beam characteristic. The light is generated on electrodes such that the light is generated across a certain spatial area. Thus, certain areas of light source 1 are hotter than others. In addition, the discharge processes at the electrodes are subject to temporal fluctuations, such that, on the whole, the entire beam characteristic is subject to variations in intensity.

Typically, light source 1 has a relatively small area of maximum temperature, the hot spot. Since beam characteristic is relative stable here, the light radiated from this hot spot is particularly suitable for ellipsometric purposes.

By means of first aperture 2, which is arranged in the light path of the emitter light beam 3A, it is possible to select a specific portion of light source 1. Thus, in a simple manner, an emitter light beam 3A with particularly defined characteristics is obtained.

Because the stability of the light source also depends on its position, the light source can be moved into the light path by means of plane mirrors, such that the lamp can be operated in an optimal position with regard to its stability.

Downstream from first aperture 2, emitter light beam 3A passes through a first polarization optic 4. First polarization optic 4 generates a defined polarization condition in emitter light beam 3A. It is, in principle, possible to use linear, elliptic or circular polarization. Also, first polarization optic 4 can be arranged fixedly in relation to emitter light beam 3A or can rotate around it. The first polarization optic 4 that is used here has especially low beam deflection such that the measuring spot remains at the same place, regardless of the rotational status of first polarization optic 4.

Emitter light beam 3A is focused via an emitter lens system 5 onto a particularly small measuring spot ($\mu$spot, microspot) of sample 50. The optic of emitter lens system 5 is designed such that it is suitable for polarization-optical measurements. In the present case, a lens triplet with high achromatism is used. The aperture of emitter lens system 5 is designed such that at least the first diffraction order generated downstream from first aperture 2 is detected. Thus, the light entering through first aperture 2 is imaged on the measuring spot of sample 50 with high quality.

After the reflection of emitter light beam 3A on sample 50, the resulting receiver light beam 3B is routed through a receiver lens system 6 and via a second polarization optic 7 to a detector 8 to evaluate the polarization condition of receiver light beam 3B. It is possible to design second polarization optic 7 stationary or rotating around receiver light beam 3B.

The ellipsometer of the present invention uses a second polarization optic 7 with two modes of operation. In one mode, second polarization optic 7 is continuously in motion, enabling very short measuring times. A second mode allows measurements at various, pre-determined positions of second polarization optic 7, at which positions second polarization optic 7 does not move during the measurement. This mode can be used for samples with low reflectivity to increase measuring accuracy. These two modes of operation are also used in alternative embodiments with first polarization optic 4.

Using a dispersive element with an entrance slit (not shown), which dispersive element is arranged in front of detector 8, the light beam is dispersed into its spectral components, and the intensities of the various wavelengths can be determined consecutively or simultaneously by a suitable detector.

If dispersive element 17 images the axis of the entrance slit parallel to the incidence plane in the detector plane, or if an additional optical system performs this imaging, it is possible to analyze angle-dependent data, using a two-dimensional detector 8. For example, a two-dimensional photo diode array can be used for this.

Thus, even multi-angle analysis of the reflected light is possible. Downstream from the focusing emitter lens system 4, broadband emitter light beam 3A strikes sample 50 at different angles and is reflected at the corresponding different angles as receiver light beam 3B; thus, the angle information is contained in receiver light beam 3B. Behind the entrance slit of a spectrometer 17, two-dimensional detector 8 can perform a spectroscopic analysis of respective light beams that were beamed onto sample 50 at different angles.

In an alternative embodiment, spectrometer 17 is equipped with a multichannel detector to increase the measuring speed. This arrangement enables fast measurement of light intensities across the wavelength range used.

It is also possible to direct emitter light beam 3A at different angles onto sample 50 by pivoting the emission arm of the ellipsometer with light source 1. Using this method, light beams of different angles are also beamed onto the sample. A two-dimensional detector 8 then allows the appropriate analysis.

This is the basic configuration of an embodiment of the ellipsometer of the present invention with a refraction optic for generating the measuring spot.

Figure 2:
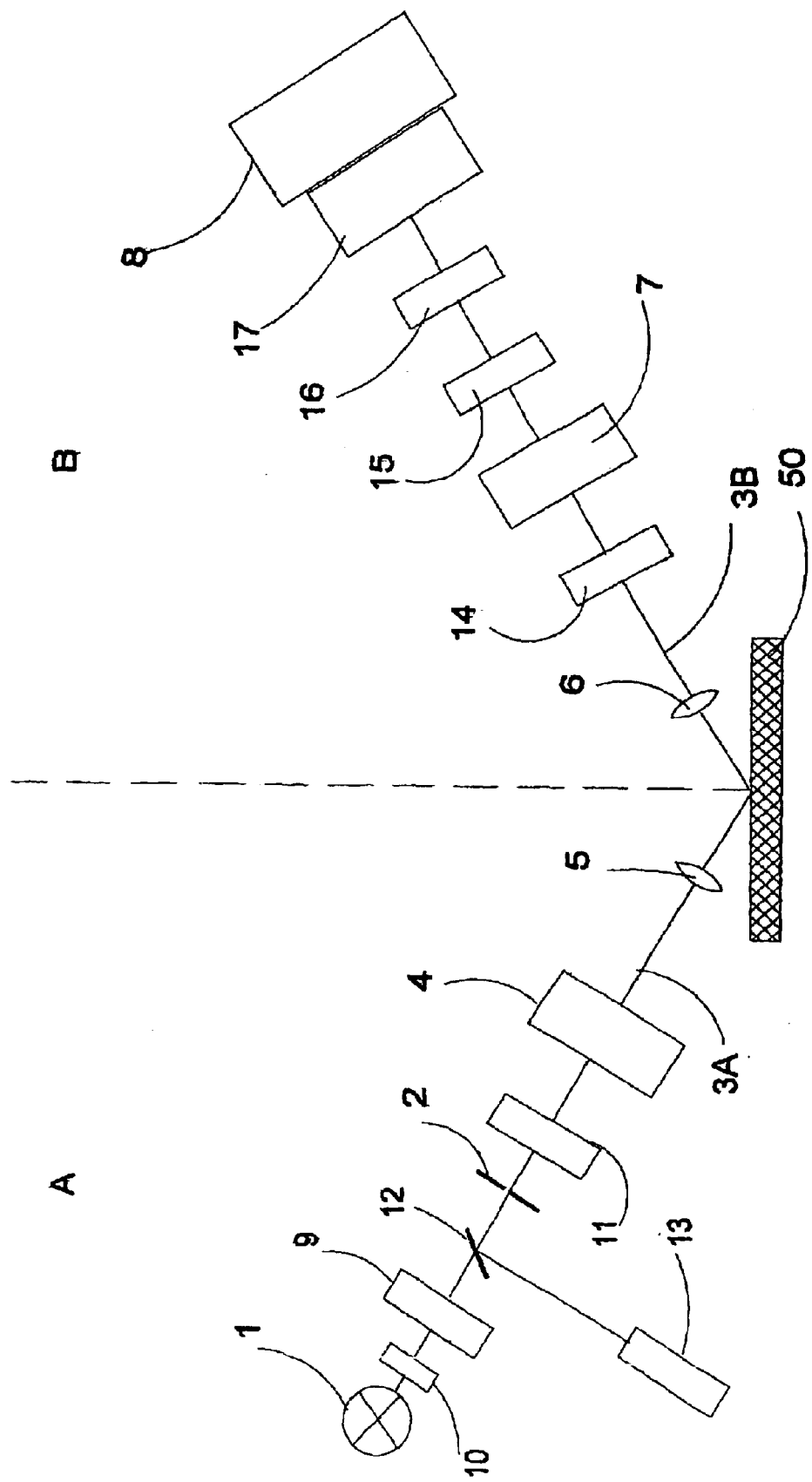
FIG. 2 is a schematic view of an embodiment of the ellipsometer of the present invention.

FIG. 2 depicts an embodiment of the ellipsometer of the present invention that provides additional components. These components can be used individually or in different combinations with the ellipsometer of the present invention. Here, the components already depicted in FIG. 1 have the same reference characters, making it possible to refer to the corresponding description of FIG. 1.

In the embodiment according to FIG. 2, a convex lens 10 that focuses emitter light beam 3A is arranged behind light source 1. A yellow filter 9, pivotable into the beam path, is arranged behind the convex filter. A laser beam of a discrete wavelength ellipsometer 13 (DWE) is coupled parallel to emitter light beam 3A via a stationary beam splitter 12. In first aperture 2, both beams undergo the same beam forming. In FIG. 2, the two beams are depicted above each other as one beam. In particular, both beams are reflected at the same measuring spot on sample 50, such that the laser beam of discrete wavelength ellipsometer 13 is also parallel to receiver light beam 3B.

The laser beam of discrete wavelength ellipsometer 13 uses the same optical components and polarization optics as emitter light beam 3A and receiver light beam 3B.

The light source of discrete wavelength ellipsometer 13 (in this case a laser diode) has better stability than broadband light source 1, such that the quality of the measurements of the ellipsometer of the present invention is further improved. The laser beam is evaluated on a photo diode of a laser detector 15, which has higher measuring accuracy than the multi-wavelength detector.

In addition to improving the measurements, the laser beam of discrete wavelength ellipsometer 13 is also used for adjustment and verification purposes for the calibration of the ellipsometer of the present invention.

Furthermore, in this embodiment a grey filter changer 11 is arranged behind first aperture 2. This grey filter is used to adjust the intensity of emitter light beam 3A (and, optionally, of the laser beam of discrete wavelength ellipsometer 13) to the reflectivity of various samples 50. For this purpose, grey filter changer 11 has various grey filters that are arranged in tandem and provide multiplied transmissivity. The combination of the grey filters is achieved by computer control of the ellipsometer (not shown).

In addition, a retarder 14 on receiver side B can be pivoted into receiver light beam 3B to generate a phase shift.

In principle, ellipsometers have the problem that the detector signal and/or the transmission of the dispersive element (for instance, a grid of a spectrometer) depends on the polarization condition. These effects impact the measuring results, because actually only the changes in the polarization condition downstream from the reflection on sample 50 are supposed to be measured. A correction is necessary if the polarization itself influences the measurement.

The ellipsometer of the present invention allows particularly easy correction of the polarization dependency by performing a reference measurement of a quartz sample with a known refraction index. This uses the following steps:
1. First, the angle of incidence on the sample is determined, with no correction values taken into consideration yet.
2. Then, the ellipsometric angle PSI is calculated for this angle of incidence and for all wavelengths of the polychromatic light.
3. The rotation of the polarization axes behind the quartz sample is calculated based on these calculated angles. This makes it possible to use the polarizer setting to ascertain the dependency of the polarization axes downstream from the sample.
4. Then, first polarization optic 4 is moved such that almost equidistant polarization axes are generated behind the quartz sample. The modulation factor or the remaining value is measured.

This requires a certain number of steps or resolution of the polarization optic (for instance, 6400 steps).

5. According to a Russev method (App. Optics vol. 28, no. 8, April 1989, page 1504–1507, the contents of which are incorporated by reference herein), correction values for all wavelengths are calculated by means of a Fourier analysis of the modulation factor.
6. Then, the polarizer offset of the first polarization optic is determined and the appropriate corrections are performed.

The polarization offset is the distance between the polarization axis and the incidence plane, when the drive of the polarization optic is located in its reference.

7. Steps 1 through 6, or 6, are repeated until the incidence angle and/or the polarizer offset of first polarization optic 4 no longer change noticeably.

This method makes it possible to calibrate an ellipsometer of the present invention even on site.

FIG. 3 depicts details of the lamp exchange mentioned above. Light sources 1, 1' are arranged in a lamp housing 32. Light source 1, depicted in emitter beam path 3A in the drawing, is called the active light source. The other five light sources 1' are not active in the position depicted in FIG. 3, i.e., they serve as backup light sources in case active light source 1 fails. Light sources 1, 1' are arranged on a rotatable table 40 as a positioning means. Rotatable table 40 can be rotated (in the direction of the arrow) by drive 34, to move light sources 1, 1' into a different position relative to emitter beam path 3A.

Rotatable table 40 has a reflector 31 that concentrates the light that is emitted from active light source 1 and focuses it again in the direction of emitter light beam 3A. Thus, the light of light source 1 is better utilized. Here, reflector 31 is designed as a spherical mirror whose distance from the active light source can be adjusted to adapt the mirror to various operating conditions.

In the embodiment shown, a portion of emitter light beam 3A is guided to sensor 19 via beam splitter 20. Among other things, sensor 19 measures the intensity of the light beam. Depending on the measuring result of sensor 19, the spatial position of light source 1 is changed (for instance, shifted up or down, left or right, tilting of the light source), until a particularly good beam characteristic is achieved. Similarly, reflector 31 is also adjustable depending on the measuring results, to obtain the best possible beam characteristic.

FIG. 4 depicts a schematic side view of a lamp changer. Light sources 1, 1' are rotatably arranged in lamp housing 32 on rotary table 40 around a rotation axis 41, whereby drive 34 provides the necessary torque, when one of light sources 1, 1' is to be rotated into a different position. An ignition element 33 serves as the power supply for respective active light source 1.

In the embodiment depicted here, a three-axis test table 42 is used for the spatial positioning of active light source 1. By adjusting the inclination of test table 42, it is possible in each instance to move a different illuminating area of active light source 1 into emitter beam path 3A.

The practice of the present invention is not limited to the above-reported preferred embodiments. On the contrary, a number of alternatives are conceivable using the ellipsometer of the present invention even in embodiments that are significantly different.

Furthermore, the terms for the geometric data, such as "perpendicular", "parallel", "square", "rectangular", are to be understood such that minor deviations from the theoretically ideal geometrical relation among the components are included.

What is claimed is:

1. Ellipsometer for examination of a sample, comprising:
   a broadband light source on an emitter side of the ellipsometer;
   a detector for a receiver light beam reflected by the sample on a receiver side of the ellipsometer; and
   a refractive optic for the generation of a measuring spot on the sample, including a field aperture having an opening arranged on the emitter side for definition of a measuring spot on the sample, an emitter lens system for focusing of the light beam on the sample, wherein the aperture of the emitter lens system is configured such that at least the first diffraction order is detected downstream from the field aperture.

2. Ellipsometer according to claim 1, wherein at least one of the emitter lens system and a receiver lens system has at least one achromatic lens system.

3. Ellipsometer according to claim 2, wherein the emitter lens system and the receiver lens system are designed such that the ellipsometric angles PSI and DELTA in an arrangement where the ellipsometer arms are each at 90°, i.e., in the transmitted light position, are influenced only below the precision limit of the ellipsometer if at least one lens system is inserted when the aperture of at least one of the lens systems is fully illuminated.

4. Ellipsometer according to claim 1, further comprising means for the imaging of a hot spot of the light source in the plane of a lens of the emitter lens system.

5. Ellipsometer according to claim 1, wherein the opening of the aperture is directed to a hot spot of the light source.

6. Ellipsometer according to claim 1, wherein the opening of the aperture has a rectangular shape.

7. Ellipsometer according to claim 1, wherein the opening of the aperture has adjustable geometry.

8. Ellipsometer according to claim 1, wherein the longest axis of the opening of the aperture is perpendicular to the incidence plane of the emitter light beam on the sample.

9. Ellipsometer according to claim 1, wherein the light source has electrodes and a connecting line of the electrodes is arranged parallel to longest axis of the opening of the aperture.

10. Ellipsometer according to claim 1, wherein the light source has electrodes and a connecting line of the electrodes is arranged perpendicular to longest axis of the opening of the aperture.

11. Ellipsometer according to claim 1, further comprising at least one retarder pivoted into a corresponding light path for the phase shift of at least one of the emitter light beam and the receiver light beam.

12. Ellipsometer according to claim 11, wherein the at least one retarder is an achromatic retarder.

13. Ellipsometer according to claim 11 or 12, wherein the at least one retarder is rotatable.

14. Ellipsometer according to claim 1, further comprising at least one grey filter pivotable into the emitter light path for intensity regulation.

15. Ellipsometer according to claim 1, further comprising an adjustable first polarization optic arranged on the emitter side and an adjustable second polarization optic arranged on the receiver side.

16. Ellipsometer according to claim 15, wherein the first polarization optic and the second polarization optic have a beam deflection of less than 15 arc seconds.

17. Ellipsometer according to claim 15 or 16, wherein in different measuring modes the first polarization optic and the second polarization optic are moved selectively and continuously with constant rotation speed or with measurements at various pre-determined positions.

18. Ellipsometer according to claim 2, further comprising a further aperture having an opening arranged behind the receiver lens system for the selection of the incidence angle of the reflected light beam.

19. Ellipsometer according to claim 18, wherein the further aperture has an opening with a rectangular cross-section.

20. Ellipsometer according to claim 18 or 19, wherein a longest axis of the opening of the further aperture is arranged perpendicular to an incidence plane.

21. Ellipsometer according to claim 18, wherein the detector for the receiver light beam reflected by the sample is coupled to a spectrometer, and the entrance slit of the spectrometer is arranged perpendicular to a longest axis of the opening of the further aperture.

22. Ellipsometer according to claim 21, wherein the spectrometer images the entrance slit in the detector plane retaining the image in the longitudinal direction of the entrance slit as well.

23. Ellipsometer according to claim 21, further comprising an optical system for the imaging of the entrance slit into the detector plane.

24. Ellipsometer according to claim 21, wherein the imaging of the entrance slit in the detector plane takes place by means of a dispersive element of the spectrometer itself.

25. Ellipsometer according to claim 21, further comprising a two-dimensional detector for the evaluation of the angle-dependent data.

26. Ellipsometer according to claim 25, wherein the detector has a two-dimensional FFT CCD, a matrix of single diodes, PMTs or at least two one-dimensional photo diode arrays.

27. Ellipsometer according to claim 18, wherein the detector for the receiver light beam reflected by the sample is coupled to a grid spectrometer, and the grid is arranged such that the grid lines are arranged perpendicular to the longest axis of the further aperture-imaged in the beam direction.

28. Ellipsometer according to claim 1, further comprising a quartz sample or a sample with a phase shift of near 0° or near 180° for the determination of the correction of the polarization sensitivity of the detector and/or the spectrometer over a sample.

29. Ellipsometer according to claim 1, further comprising a discrete wavelength ellipsometer with a laser as a light source, wherein the beam of the laser uses the same path as the broadband light beam.

30. Ellipsometer according to claim 29, wherein the laser beam of the discrete wavelength ellipsometer is reflected into the light path of the ellipsometer by a beam splitter.

31. Ellipsometer according to claim 29 or 30, further comprising an aperture structure switches over between the laser beam and the discrete wavelength ellipsometer and the broadband light beam.

32. Ellipsometer according to claim 29, further comprising a low-noise detector coupled to the receiver light beam via a beam splitter.

33. Ellipsometer according to claim 29, wherein the laser beam of the discrete wavelength ellipsometer is used for the adjustment of the ellipsometer.

34. Ellipsometer according to claim 1, further comprising at least one sensor-in at least one of the emitter light path and in the receiver beam path for intensity and position control of the light source.

35. Ellipsometer according to claim 34, wherein the sensor is arranged behind the aperture.

36. Ellipsometer according to claim 1, further comprising at least one-activatable changer for at least one light source.

37. Ellipsometer according to claim 36, wherein the changer has a rotating table.

38. Ellipsometer according to claim 36 or 37, wherein the at least one light source of the changer is preadjusted.

39. Ellipsometer according to claim 36, wherein the changer has at least one manually or automatically adjustable reflector for the respective active light source.

40. Ellipsometer according to claim 1, further comprising: means for automatic control of the respective active light source.

41. Ellipsometer for examination of a sample, comprising:
a broadband light source on an emitter side of the ellipsometer;
a detector for a receiver light beam reflected by the sample on a receiver side of the ellipsometer;
a refractive optic for the generation of a measuring spot on the sample, including a field aperture having an opening arranged on the emitter side for the definition of a measuring spot on the sample, an emitter lens system for focusing of the light beam on the sample, wherein the aperture of the emitter lens system is configured such that at least the first diffraction order is detected downstream from the field aperture; and
a positioning means for spatial positioning of at least one light source with reference to the light path.

42. Ellipsometer according to claim 41, wherein the positioning means has a three-axis test table.

43. Ellipsometer according to claim 41 or 42, wherein the spatial position of at least one of the light source and the reflector is adjustable based on at least one regulating variable.

44. Ellipsometer according to claim 43, wherein at least one regulating variable is generated by the sensor.

45. Ellipsometer for examination of a sample, comprising:
a broadband light source on an emitter side of the ellipsometer;
a detector for a receiver light beam reflected by the sample on a receiver side of the ellipsometer; and
a refractive optic for the generation of a measuring spot on the sample, including a field aperture having an opening arranged on the emitter side for the definition of a measuring spot on the sample, an emitter lens system for focusing of the light beam on the sample, wherein the aperture of the emitter lens system is configured such that at least the first diffraction order is detected downstream from the field aperture, wherein a light source is reflected via at least one mirror into the light path such that the light source is perpendicular to it.

* * * * *